US011491070B2

(12) United States Patent
Fox

(10) Patent No.: US 11,491,070 B2
(45) Date of Patent: Nov. 8, 2022

(54) SPINE BOARD

(71) Applicant: Richard J. Fox, Edmonton (CA)

(72) Inventor: Richard J. Fox, Edmonton (CA)

(*) Notice: Subject to any disclaimer, the term of this patent is extended or adjusted under 35 U.S.C. 154(b) by 610 days.

(21) Appl. No.: 16/592,533

(22) Filed: Oct. 3, 2019

(65) Prior Publication Data
US 2020/0107985 A1    Apr. 9, 2020

Related U.S. Application Data

(60) Provisional application No. 62/741,074, filed on Oct. 4, 2018.

(51) Int. Cl.
*A61H 1/02*    (2006.01)
*A61G 1/04*    (2006.01)

(52) U.S. Cl.
CPC ............ *A61H 1/0222* (2013.01); *A61G 1/04* (2013.01); *A61G 2203/20* (2013.01); *A61H 2201/0134* (2013.01); *A61H 2201/163* (2013.01); *A61H 2201/1607* (2013.01); *A61H 2201/1611* (2013.01); *A61H 2201/1626* (2013.01); *A61H 2201/1664* (2013.01); *A61H 2201/5043* (2013.01)

(58) Field of Classification Search
CPC .... A61H 1/0222; A61H 1/0292; A61G 7/103; A61G 1/04; A61G 1/042; A61G 1/044; A61G 1/00; A61G 13/02; A61G 13/04; A61G 13/06; A61G 13/08
See application file for complete search history.

(56) References Cited

U.S. PATENT DOCUMENTS

| | | | |
|---|---|---|---|
| 3,009,461 A | 11/1961 | Collins | |
| 3,046,982 A | 7/1962 | Davis | |
| 3,139,883 A | 7/1964 | Collins | |
| 3,662,750 A | 5/1972 | Jorgensen | |
| 3,811,433 A | 5/1974 | Brachet | |
| 3,868,951 A | 3/1975 | Albrecht | |
| 4,220,147 A | 9/1980 | Allen, III | |
| 4,257,410 A | 3/1981 | Flewelling | |
| 4,473,912 A | 10/1984 | Scheidel et al. | |
| 4,489,715 A | 12/1984 | Hall | |
| 4,566,445 A | 1/1986 | Jelsma et al. | |
| 4,854,305 A | 8/1989 | Bremer | |
| 4,890,605 A * | 1/1990 | Rosendale | ........... A61H 1/0218 602/33 |
| 5,088,137 A | 2/1992 | Rose | |
| 5,819,746 A | 10/1998 | Walton | |
| 5,865,780 A | 2/1999 | Tuite | |

(Continued)

FOREIGN PATENT DOCUMENTS

WO    WO-2017098463 A1 *    6/2017 ............... A61F 5/04

*Primary Examiner* — Joseph D. Boecker
*Assistant Examiner* — Thomas W Greig
(74) *Attorney, Agent, or Firm* — Foley & Lardner LLP

(57) ABSTRACT

A spine board is provided having a skull tong anchor assembly slidably attached to the spine board where a push rod mechanism is used to apply traction force on the skull tong anchor assembly. The push rod mechanism includes a strain gauge device so that the traction force can be selected and monitored. The spine board can also include a mattress that can be attached to the spine board where the mattress includes integrated shoulder straps that can be partially detached therefrom to secure a patient to the spine board.

19 Claims, 20 Drawing Sheets

(56) References Cited

U.S. PATENT DOCUMENTS

| | | | | |
|---|---|---|---|---|
| 6,113,563 | A * | 9/2000 | D'Amico | A61H 1/0296 |
| | | | | 602/33 |
| 7,082,632 | B2 | 8/2006 | Hood | |
| 2011/0270310 | A1* | 11/2011 | Dyer | A61H 1/0222 |
| | | | | 606/242 |
| 2013/0131570 | A1* | 5/2013 | Hoffman | A61F 5/3707 |
| | | | | 602/36 |
| 2014/0188027 | A1* | 7/2014 | Jaber | A61F 5/048 |
| | | | | 602/36 |
| 2015/0202111 | A1* | 7/2015 | Byrd | A61H 1/0222 |
| | | | | 606/240 |
| 2017/0239127 | A1* | 8/2017 | Park | A61H 1/0292 |

* cited by examiner

SPINE BOARD

CROSS-REFERENCE TO RELATED APPLICATIONS

This application claims priority of U.S. Provisional Patent Application Ser. No. 62/741,074 filed Oct. 4, 2018, which is incorporated by reference into this application in its entirety.

TECHNICAL FIELD

The present disclosure is related to the field of spine boards, in particular, spine boards for use with trauma patients requiring short-term cervical traction and inter- or intra-hospital transfers.

BACKGROUND

Trauma patients suffering from a back or neck injury need to be handled with great care when being transported to a medical facility for treatment. In some instances, it may be necessary to employ cervical traction on the patient to stabilize them when being transported.

It is, therefore, desirable to provide a spine board that can be quickly deployed by medical personnel for use with a patient wherein the patient can be secured to the spine board and to have cervical traction applied to them.

SUMMARY

A spine board is presented herein for trauma patients requiring short-term cervical traction who will also require inter- or intra-hospital transfers. In some embodiments, the spine board can provide very early re-alignment of cervical spine after trauma in order to initiate early decompression of the cervical spinal cord. Cervical traction can provide immediate realignment, as well as provide immediate improved stability to the cervical spinal column. Whereas complete reduction of cervical vertebrae, and complete decompression of the spinal cord may not be achieved with traction alone, the simplicity and expediency of the spine board presented herein can make it an attractive initial part of treatment in acute spinal cord injury. A self-contained traction device disposed thereon can allow imaging and transportation of the patient after traction is initiated, unlike conventional systems using weights, pulleys, and rope.

In some embodiments, the spine board can be an entirely self-contained device that can provide an adjustable, non-elastic, mechanical traction system with traction force measurement and digital display. The spine board can be compatible with magnetic resonance imaging ("MRI") diagnostic equipment. The spine board can be transferred between stretchers and beds, as well as in and out of diagnostic machines such as MRI and computed tomography ("CT") scanners while maintaining the patient in cervical traction. In some embodiments, the spine board can be compatible with motor vehicle, fixed wing and helicopter ambulances by being configured to be secured to the stretchers normally used in these vehicles. In some embodiments, the spine board can provide easy traction force adjustment at any time. In some embodiments, the spine board can comprise a specialized mattress system that can incorporate shoulder straps and pelvic restraint belts to maintain counter-traction during cervical traction to prevent patient movement on the spine board.

In some embodiments, this device can be designed to provide axial cervical traction in a convenient and portable fashion. It can be used for a patient with cervical malalignment and, in particular, with spinal cord injury, when the attending physician, in consultation with a spine surgeon, deems traction to be indicated.

Patients with preexisting spinal deformity require special considerations when applying cervical spine traction. Conditions such as cervicothoracic kyphosis and/or ankylosing spondylitis, for example, may preclude the patient from having traction applied with this device. Patients with stiff spines such as the elderly with advanced spondylosis may present higher risks of spinal cord injury with traction in some situations, and thus the risks and benefits must be carefully considered for each patient individually.

In some embodiments, the spine traction board can be designed to provide cervical traction for a patient who requires transportation or imaging. Once this phase of a patient's care is complete, the patient should be transferred off the board to a conventional mattress in order to avoid skin breakdown. A patient with a spinal cord injury is at high risk of skin pressure ulceration, thus, transfer off any spine board as soon as possible is recommended to prevent skin breakdown. Application of traction must always be highly tailored to the individual patient. The consulting spine surgeon will prescribe the appropriate application of cervical traction.

Broadly stated, in some embodiments, a spine board can be provided, the spine board comprising: a back board further comprising a head board cavity disposed at a head end of the back board; a head board slidably disposed in the head board cavity; a skull tong anchor assembly disposed on the head board; a traction control assembly disposed at a foot end of the back board; and at least one push rod operatively coupling the traction control assembly to the head board wherein the combination of the traction control assembly and the at least one push rod is configured to slidably extend and retract the head board within the head board cavity.

Broadly stated, in some embodiments, the spine board can further comprise track rails disposed in the head board cavity wherein the head board is slidably disposed within the track rails.

Broadly stated, in some embodiments, the skull tong anchor assembly can further comprise a post and a traveler block movably disposed on the post.

Broadly stated, in some embodiments, the skull tong anchor assembly can further comprise a rack and pinion gear mechanism operatively coupling the traveler block to the post.

Broadly stated, in some embodiments, the post can be curved in configuration.

Broadly stated, in some embodiments, the traveler block can comprise a skull tong ring.

Broadly stated, in some embodiments, the traction control assembly can further comprise: a support block disposed on the back board, the support block further comprising a threaded hole extending therethrough; a threaded rod disposed in the threaded hole; a control knob disposed on a first end of the threaded rod; and a U-joint mechanism disposed on a second end of the threaded rod, the U-joint mechanism operatively coupling the second end to the at least one push rod.

Broadly stated, in some embodiments, the at least one push rod can be disposed in a push rod cavity disposed in the back board.

Broadly stated, in some embodiments, the spine board can further comprise a first cover configured to cover the push rod cavity.

Broadly stated, in some embodiments, the at least one push rod can comprise: a lower push rod operatively coupled to the traction control assembly; an upper push rod operatively coupled to the head board; and a strain gauge operatively coupling the upper push rod to the lower push rod.

Broadly stated, in some embodiments, the strain gauge can comprise an S-type load cell.

Broadly stated, in some embodiments, the spine board can further comprise an electronic display unit operatively coupled to the strain gauge, the electronic display unit configured to visually display traction force applied to the head board by the traction control assembly.

Broadly stated, in some embodiments, the electronic display unit can be disposed in a display cavity disposed in the back board.

Broadly stated, in some embodiments, the spine board can further comprise at least one battery operatively coupled to the electronic display unit, the at least one battery disposed in a battery cavity disposed in the back board.

Broadly stated, in some embodiments, the spine board can comprise a second cover configured to cover the display cavity and the battery cavity.

Broadly stated, in some embodiments, the spine board can further comprise a mattress releasably attached to the back board with at least one strap coupled to a corresponding hand hole disposed through the back board.

Broadly stated, in some embodiments, the mattress can comprise shoulder straps configured to partially detach from the mattress, the shoulder straps configured to operatively couple to the foot end of the back board.

Broadly stated, in some embodiments, the mattress can further comprise a pelvic restraint belt.

Broadly stated, in some embodiments, the spine board can comprise at least one pelvic restraint anchor strap operatively coupling the pelvic restraint belt to the foot end of the back board.

DETAILED DESCRIPTION OF EMBODIMENTS

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments but is not necessarily included. Thus, the present technology can include a variety of combinations and/or integrations of the embodiments described herein.

Figure 1:
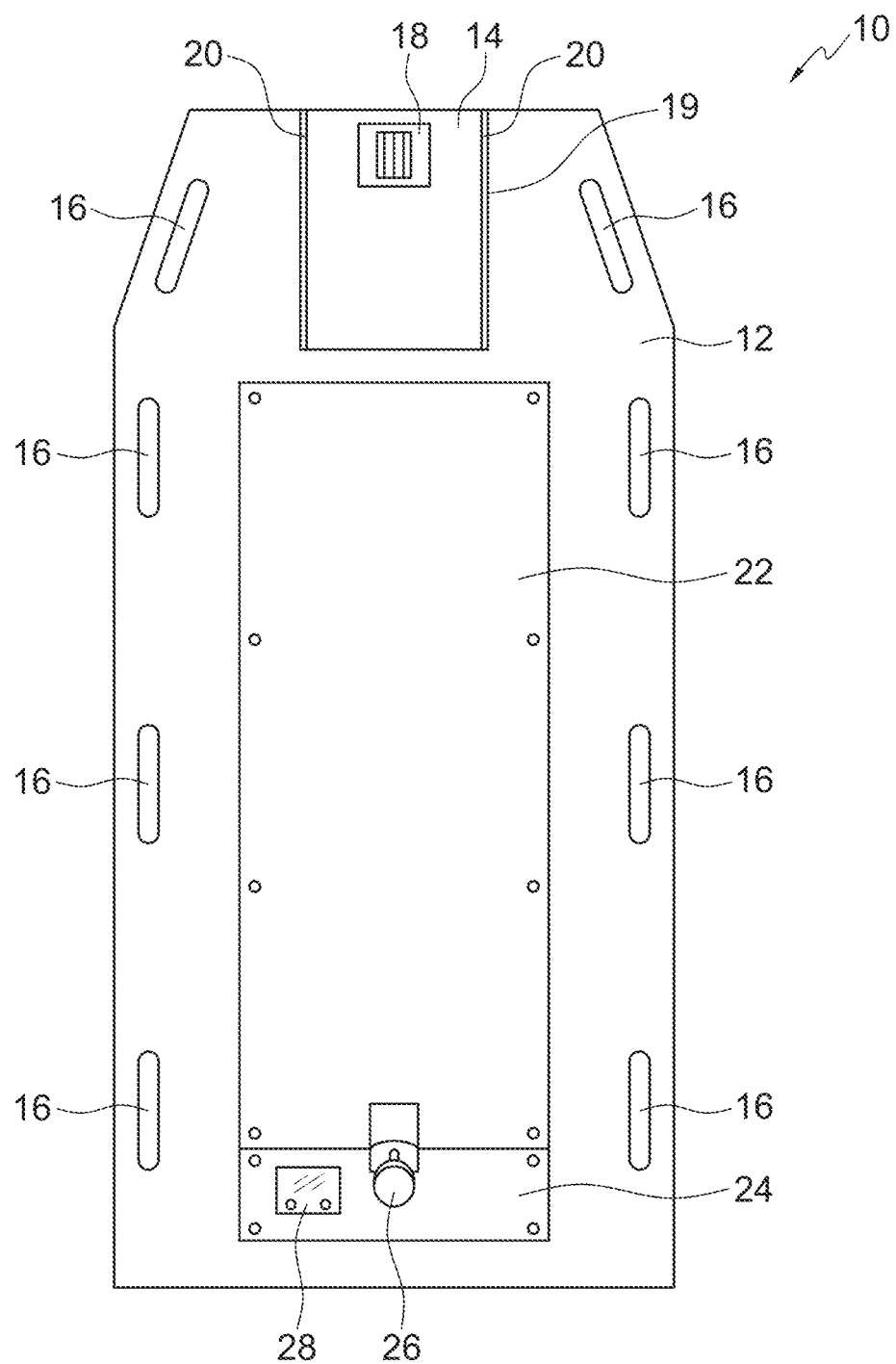
FIG. 1 is a top plan view depicting one embodiment of an improved spine board.
Figure 2:
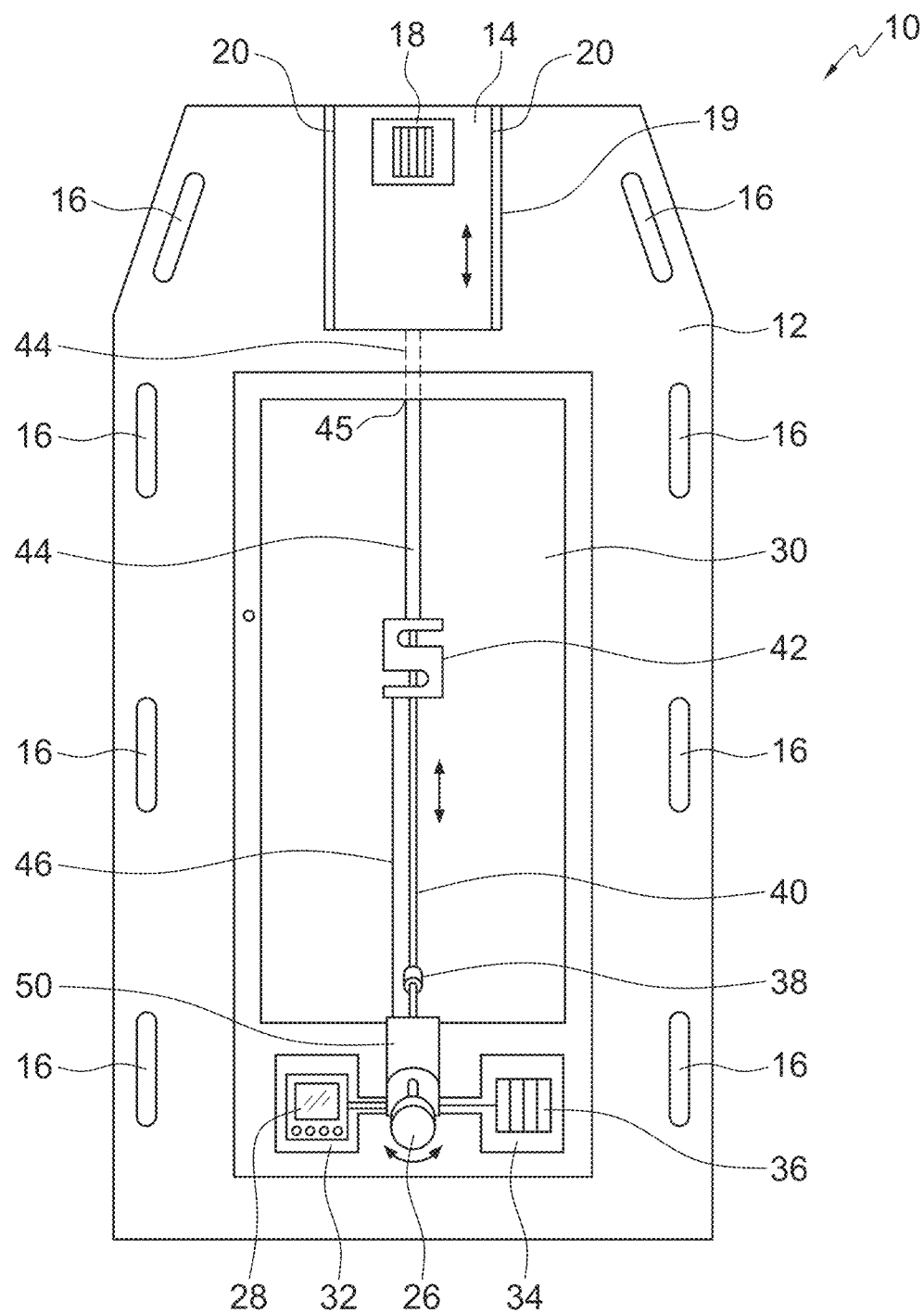
FIG. 2 is a top plan view depicting the spine board of FIG. 1 with cavity covers removed.

Referring to FIGS. 1 and 2, one embodiment of spine board 10 is shown. In some embodiments, spine board 10 can comprise of back board 12 that can comprise a plurality of hand holds 16 disposed therethrough along the sides of back board 12. In some embodiments, spine board 10 can comprise head board 14 slidably disposed in track rails 20 disposed in cavity 19 disposed at an upper or head end of back board 12, wherein head board 14 can extend outwardly along track rails 20 away from back board 12 as well as retract inwardly along track rails 20. In some embodiments, skull tong anchor assembly 18 can be disposed on head board 14.

Figure 4:
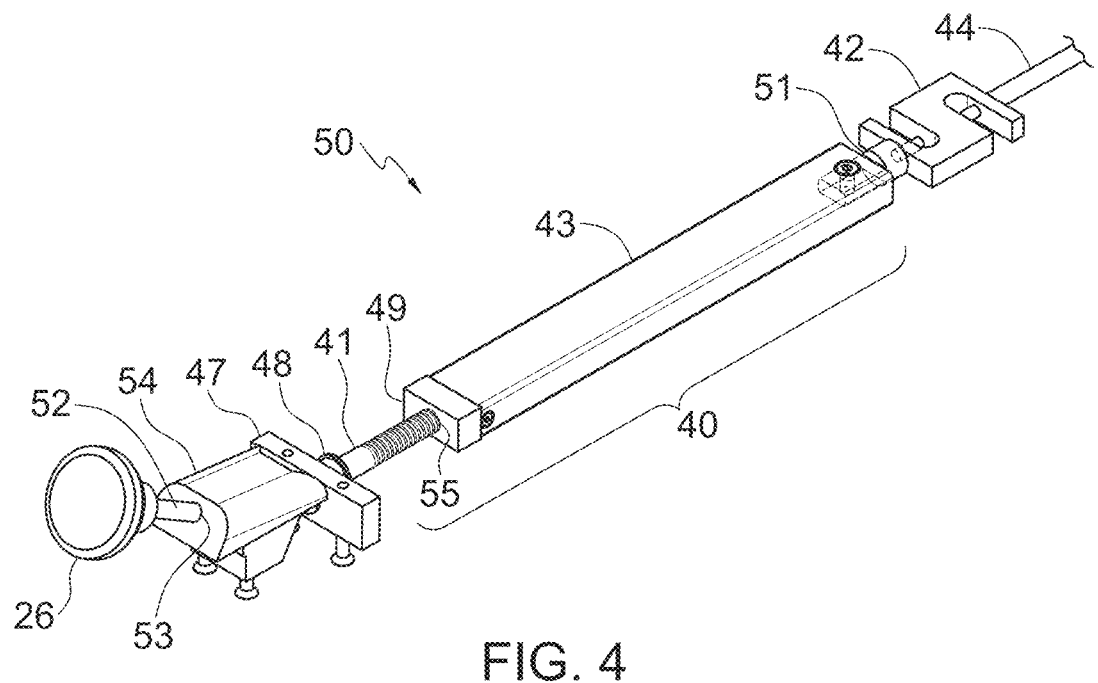
FIG. 4 is a perspective view depicting the traction control assembly of FIG. 3.

In some embodiments, spine board 10 can comprise cover 22 configured to be releasably attached to back board 12, such as with threaded connectors as well known to those skilled in the art, wherein cover 22 covers push rod cavity 30 disposed in back board 12. Spine board 10 can further comprise cover 24 releasably attached to back board 12, such as with threaded connectors, wherein cover 24 covers display cavity 32 and battery cavity 34 disposed in back board 12. In some embodiments, spine board 10 can comprise traction control assembly 50 disposed near a lower or foot end of back board 12. Traction control assembly 50 can be configured to impart a linear force on lower push rod 40 via U-joint coupler 38. Lower push rod 40 can be coupled to upper push rod 44 via strain gauge 42. In some embodiments, lower push rod 40 can be coupled to strain gauge 42 via coupler 51, as shown in FIG. 4. In some embodiments, upper push rod 44 can pass through passageway 45 disposed in back board 12 to operatively couple with head board 14. Thus, when traction control assembly 50 is adjusted with control knob 26 to impart a linear force onto lower push rod 40, the linear force transfers through strain gauge 42 to upper push rod 44 to move head board 14 along track rails 20. When a skull tong, as well known to those skilled in the art, (not shown) is connected to skull tong anchor assembly 18 and attached to a patient's head, the linear force imparted on lower and upper push rods 40 and 44 will move head board 14 to provide a traction force on the patient. In some embodiments, strain gauge 42 can be configured to measure the traction force. In some embodiments, strain gauge 42 can comprise an s-type load cell such as a JQRT series load cell available from Load Cell Central of Milan, Pa., U.S.A. In some embodiments, strain gauge 42 can comprise signal lead 46 that can couple to display unit 28 disposed in display cavity 32. Display unit 28 can comprise an RE30 load cell indicator as available from Load Cell Central of Milan, Pa., U.S.A. and can be further configured to display a numerical figure representative of the traction force being applied to the patient. Display unit 28 can be powered by one or more batteries 36 disposed in battery cavity 34.

Figure 3:
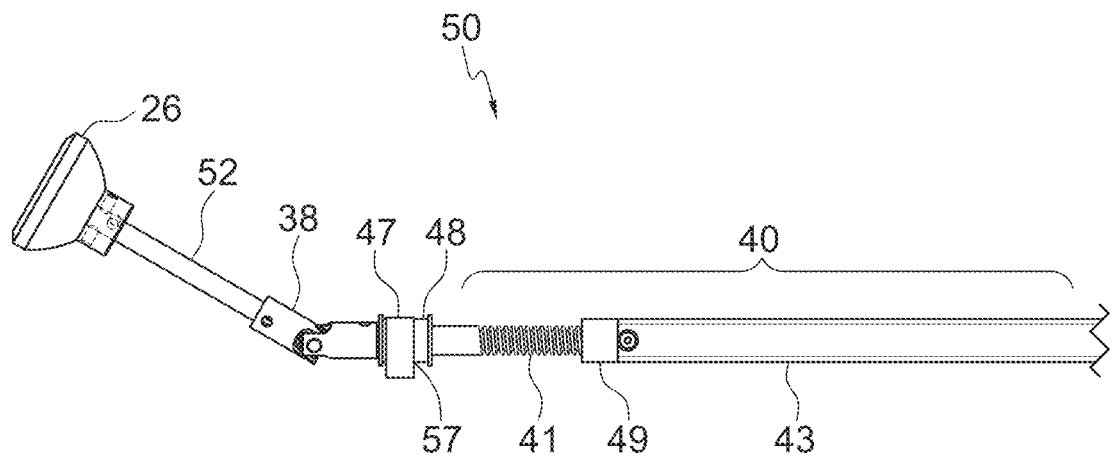
FIG. 3 is a side elevation view depicting a traction control assembly for use with the spine board of FIG. 1.

Referring to FIGS. 3 and 4, side and perspective views of one embodiment of traction control assembly 50 is shown. In some embodiments, traction control assembly 50 can comprise of support block 54 that can be attached to, or be an integral part of, back board 12. In some embodiments, traction control assembly 50 can comprise rod 52 disposed in hole 53 further disposed through support block 54. In some embodiments, push rod 40 can comprise push rod sleeve 43 further comprising insert block 49 with threaded hole 55 disposed therethrough where threaded hole 55 can be configured to threadably receive threaded rod 41. Control knob 26 can be disposed at one end of rod 52 whereas the other end of rod 52 can be operatively coupled to a first end of U-joint 38, whereas a second end of U-joint 38 can be operatively coupled to threaded rod 41. Thus, when control knob 26 is rotated, rod 52 can rotate U-joint 38 that, in turn, can rotate threaded rod 41. Threaded rod 41 can pass through bushing 48 disposed in opening 57 further disposed through block 47. As threaded rod 41 rotates, it can rotate and threadably engage with threaded hole 55 thereby imparting a linear force on push rod 40 causing push rod 40 to either move away from traction control assembly 50 or towards it, depending on the rotational direction of push rod 40.

In some embodiments, when right-handed threads are used on threaded rod 41 and threaded hole 55, rotating control knob 26 counter-clockwise can increase the traction force applied to head board 14 whereas rotating control knob 26 clockwise can decrease the traction force applied to head board 14. If left-handed threads are used for threaded rod 41 and threaded hole 55, then rotating control knob 26 clockwise can increase the traction force applied to head board 14 whereas rotating control knob 26 counter-clockwise can decrease the traction force applied to head board 14.

Figure 5:
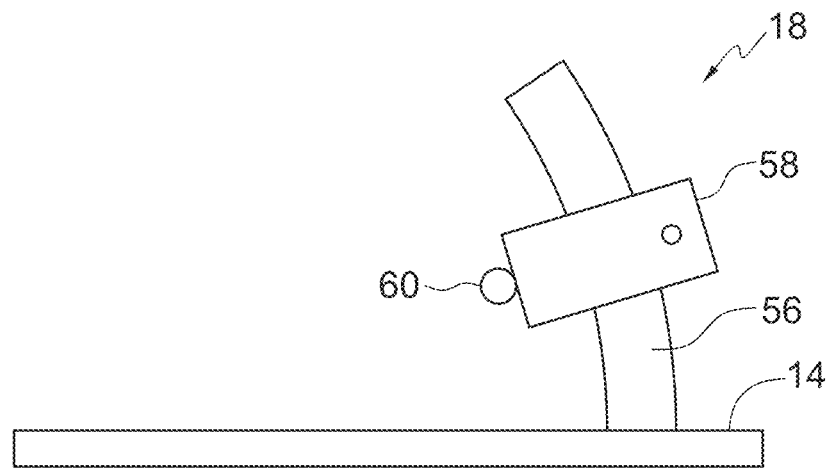
FIG. 5 is a side elevation view depicting a skull tong anchor assembly for use with the spine board of FIG. 1.
Figure 6:
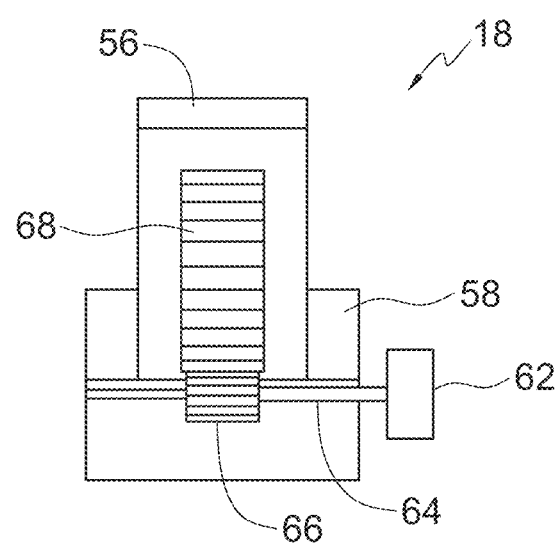
FIG. 6 is a top plan view depicting the skull tong anchor assembly of FIG. 5.

Referring to FIGS. 5 and 6, one embodiment of skull tong anchor assembly 18 is shown. In some embodiments, skull tong anchor assembly 18 can comprise of post 56 disposed on head board 14 wherein traveler block 58 is disposed on post 56. In some embodiments, post 56 can comprise rack gear 68 disposed thereon and traveler block 58 can comprise pinion gear 66 disposed on shaft 64 further comprising knob 62 disposed on an end thereof. Pinion gear 66 can engage rack gear 68 such that rotating knob 62 can cause traveler block 58 to move up or down post 56, depending on the direction knob 62 is rotated. Traveler block 58 can further comprise skull tong anchor ring 60 to which a skull tong (not shown) can be attached, as well known to those skilled in the art. In some embodiments, post 56 can be curved such that when traveler block 58 moves up or down on post 56, the traction force applied to a patient's head can remain substantially or relatively constant.

Figure 7:
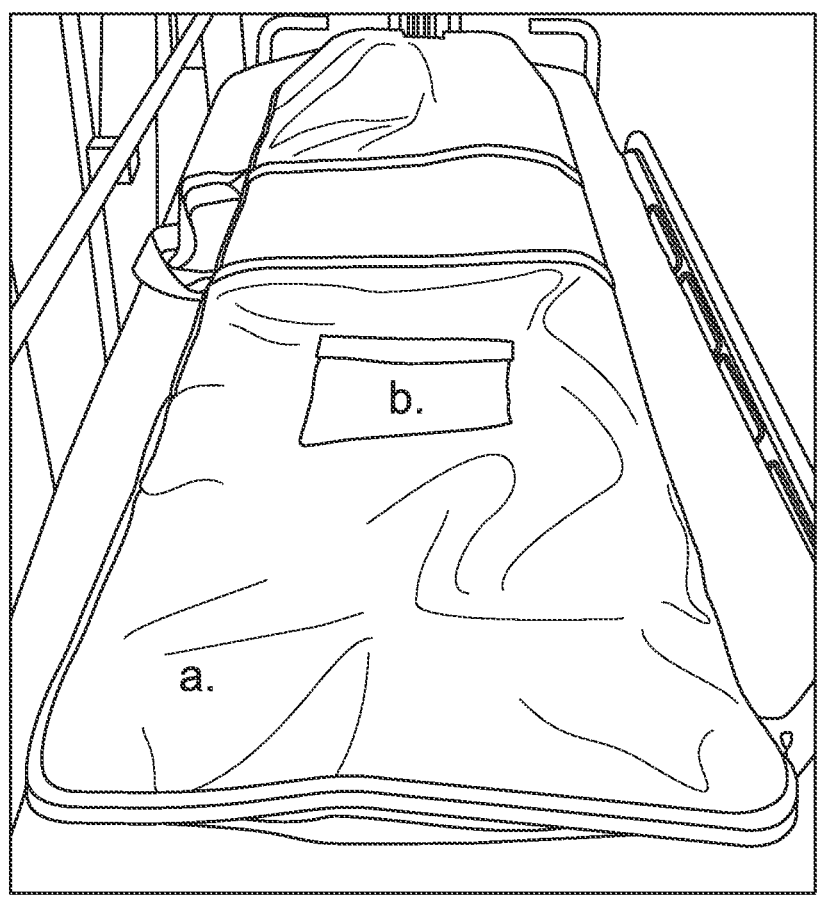
FIG. 7 is a perspective view depicting another embodiment of the spine board of FIG. 1.
Figure 8:
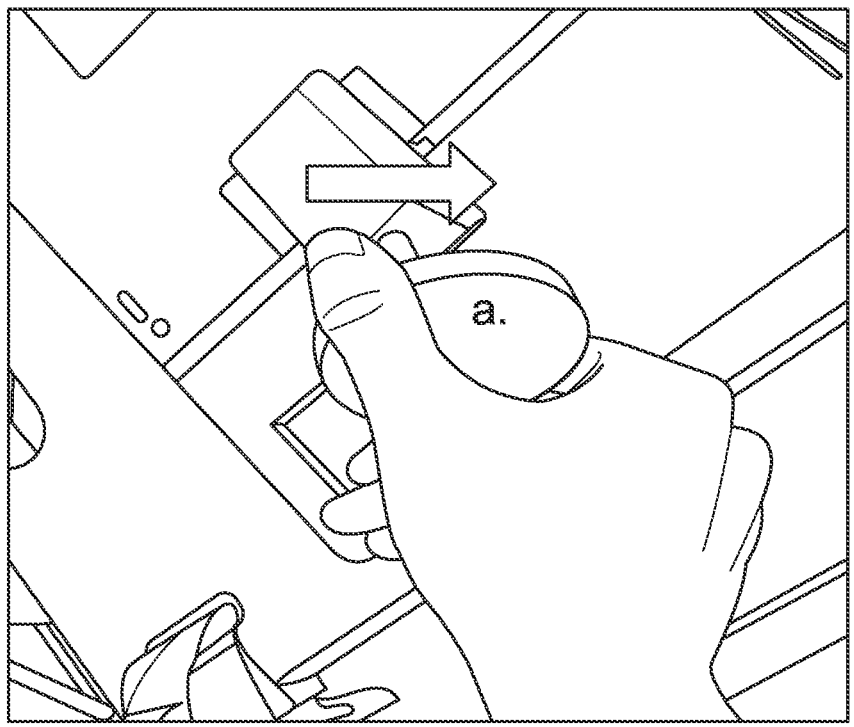
FIG. 8 is a perspective view depicting the operation of the traction control assembly of FIG. 3.
Figure 9:
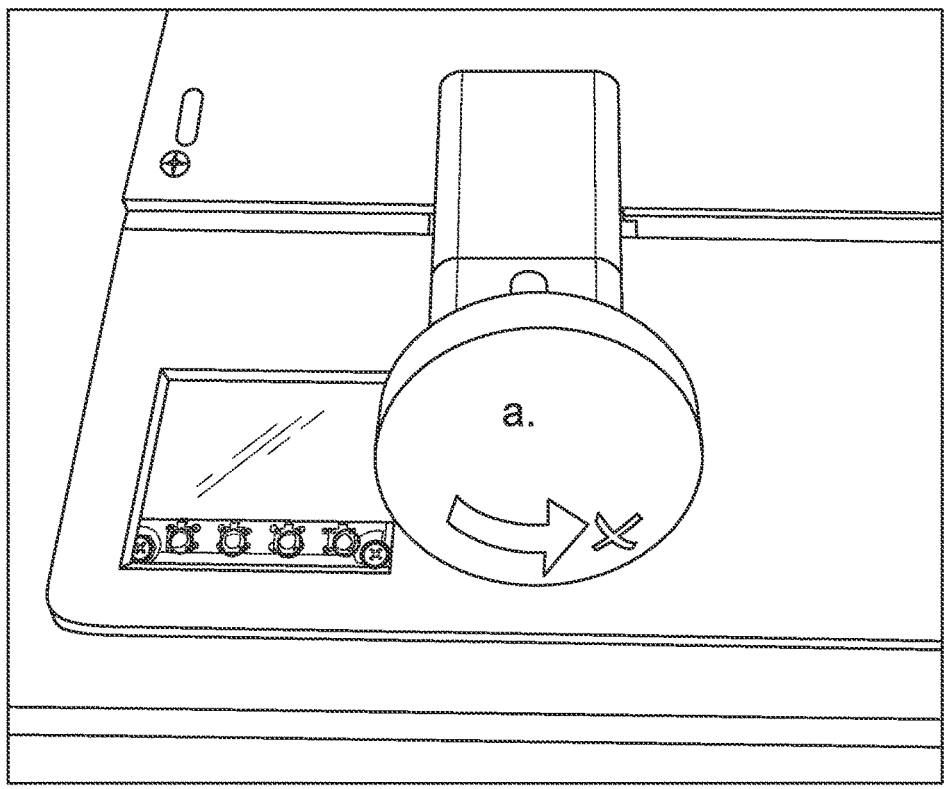
FIG. 9 is an end perspective view depicting the traction control assembly of FIG. 8.

Referring to FIG. 7, spine board can be stored and transported in a storage bag, denoted as "a.". In some embodiments, the storage bag can comprise a storage bag "b." for storing straps used to secure a patient to the spine board.

Figure 10:
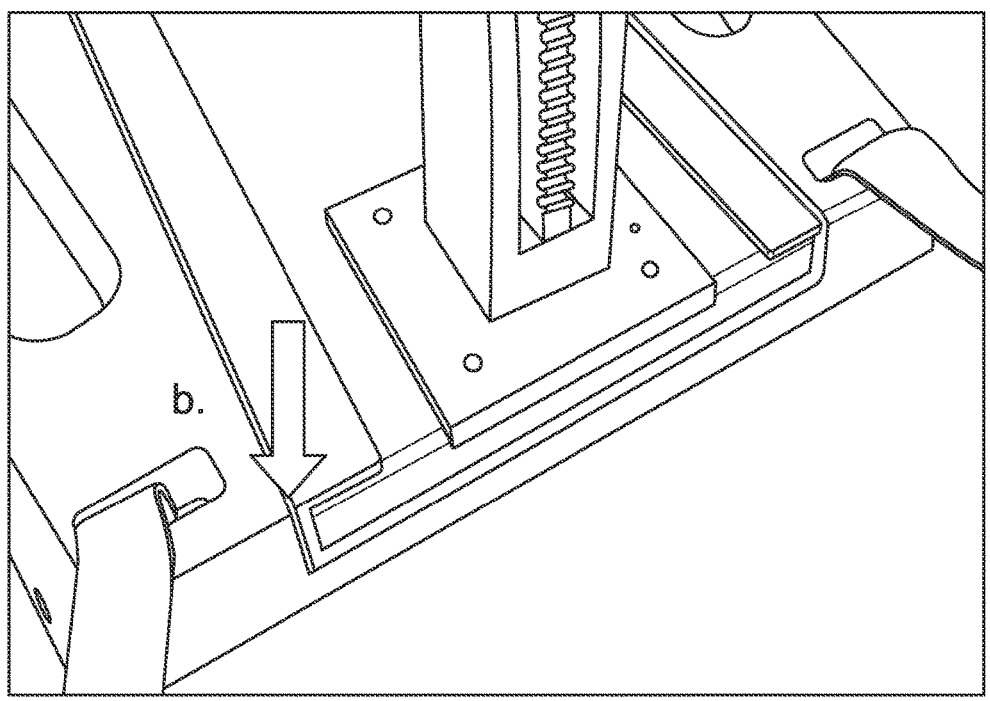
FIG. 10 is a perspective view depicting a skull tong anchor assembly fully retracted into the spine board of FIG. 7.
Figure 11:
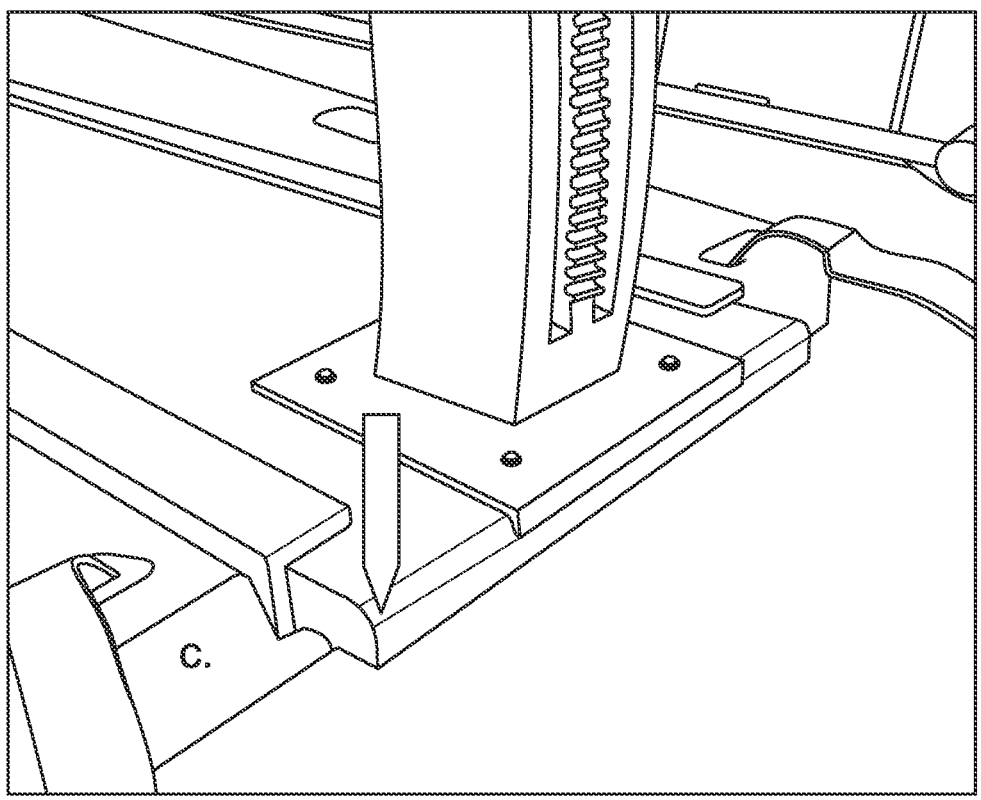
FIG. 11 is a perspective view depicting the skull tong anchor assembly of FIG. 10 extended from the spine board of FIG. 7.

Referring to FIGS. 8 to 11, rotating the traction control knob will cause the head board to move in or out. In a starting position, before a patient is placed on the spine board, if the head board is extended outward, as shown in FIG. 11, the traction knob can be rotated counter-clockwise to move the head board so that it is flush with the end of the spine board, as shown in FIG. 10.

Figure 12:
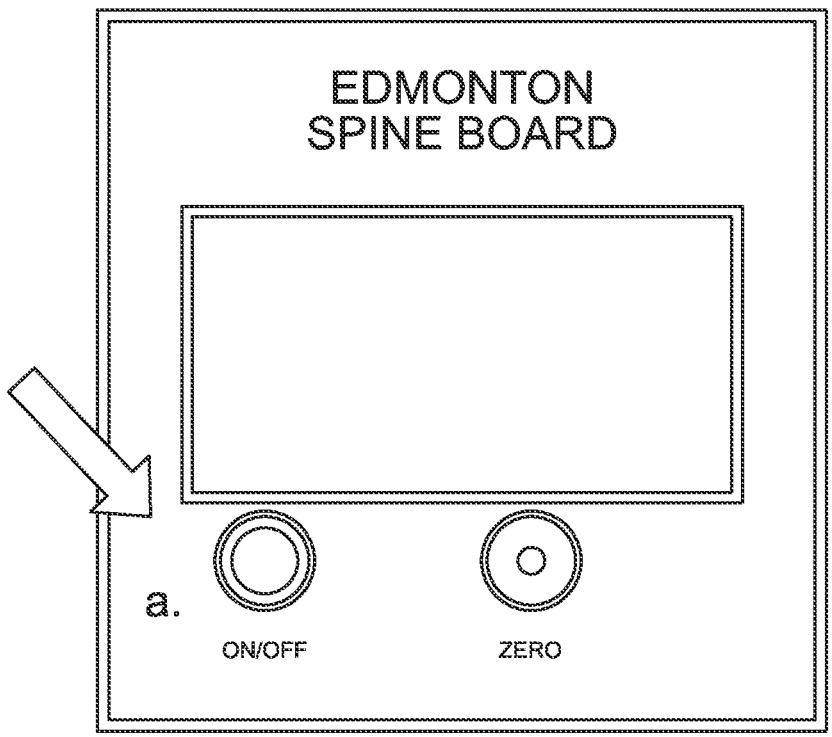
FIG. 12 is a top plan view depicting a display for use on the spine board of FIG. 1 or FIG. 7.
Figure 13:
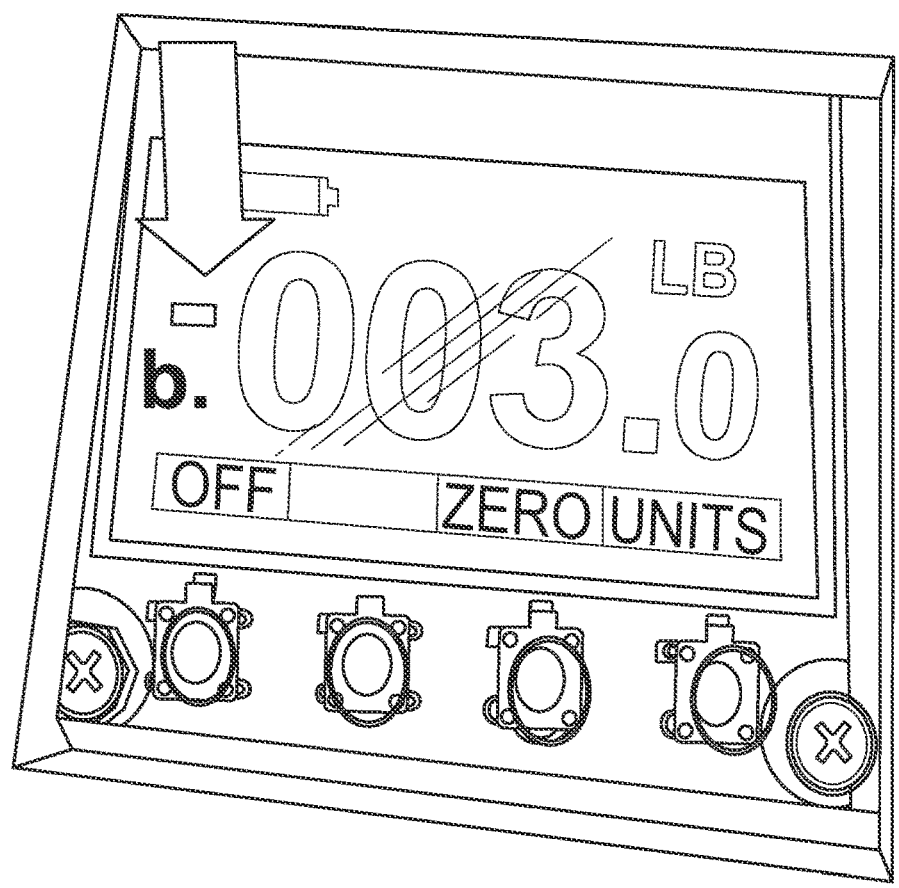
FIG. 13 is a top plan view depicting the display of FIG. 12 with its top cover removed.

Referring to FIGS. 12 and 13, the force electronic display is shown. The display unit can comprise a ON/OFF button to turn the unit on, in addition to a Zero button to "zero" the display reading before applying any traction force. As shown in FIG. 13, the display can display both negative and positive forces. If the display shows a negative, this can indicate that the head board has been retracted too far. To remedy this, the control knob can be rotated to extend the head board until the force reading nears zero.

Figure 14:
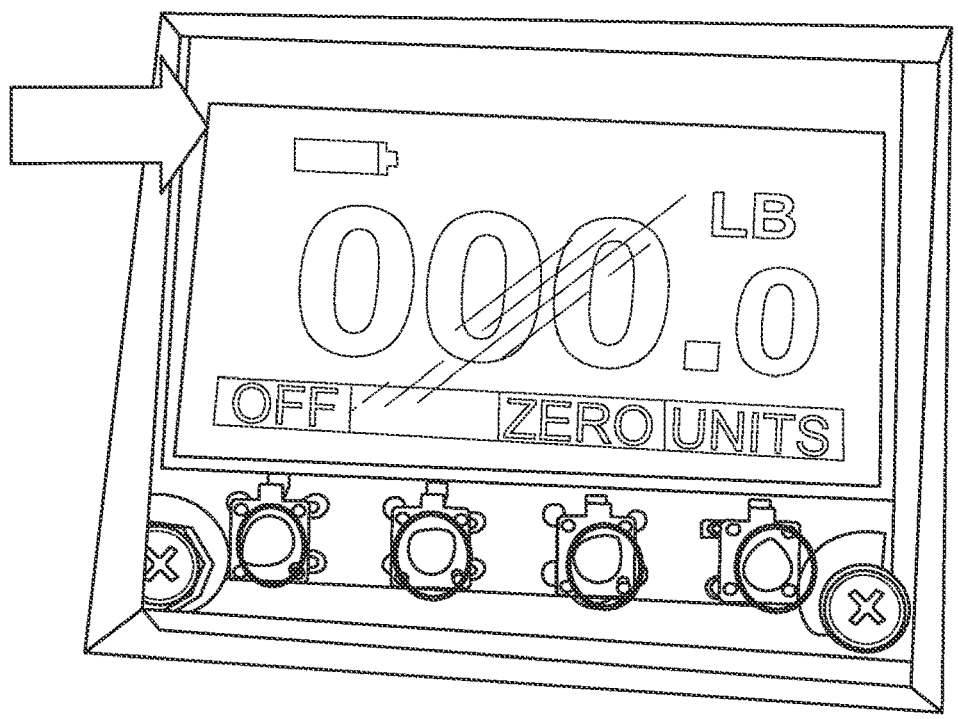
FIG. 14 is a top plan view depicting the display of FIG. 13.
Figure 15:
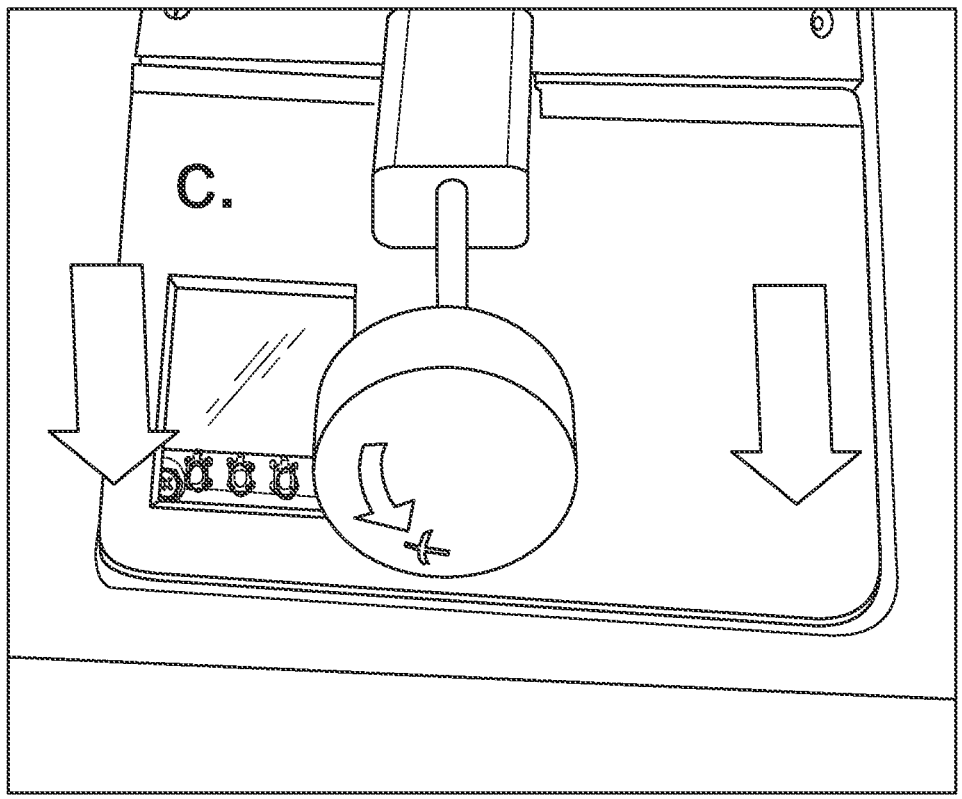
FIG. 15 is a top plan view depicting the traction control assembly of FIG. 8 with its cover being removed.
Figure 16:
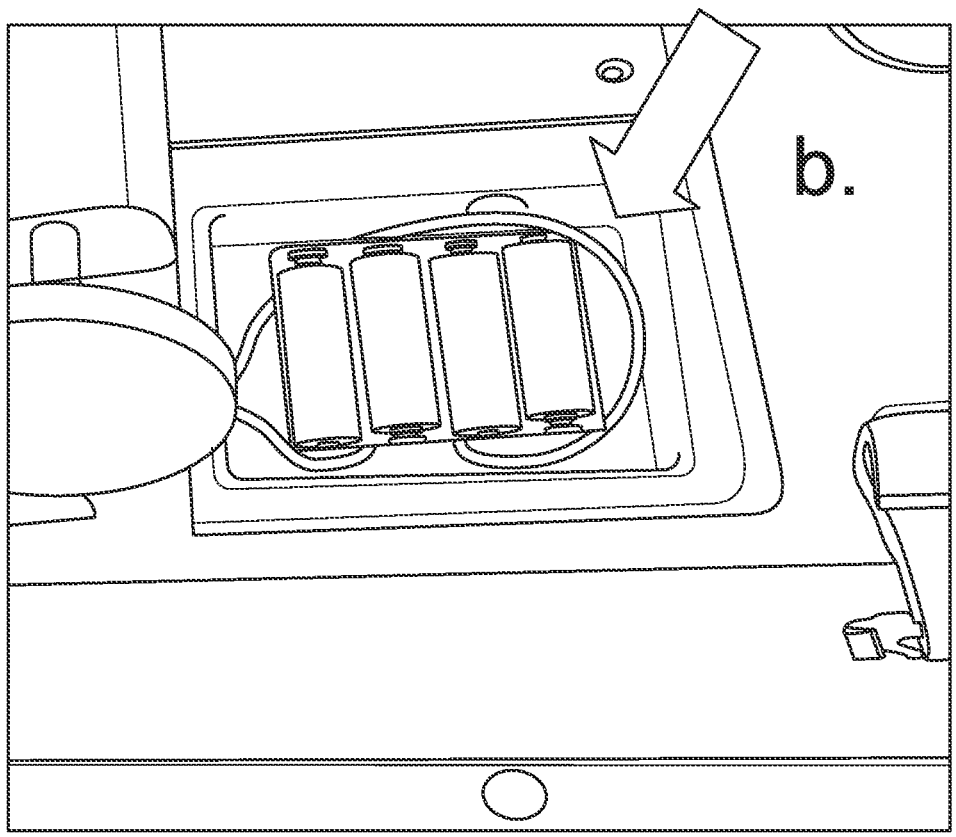
FIG. 16 is a top plan view depicting the battery cavity of the spine board of FIG. 7.

Referring to FIG. 14, the display can comprise a battery display to indicate the charge of the batteries. If the batteries become depleted, the display unit can display a "Low Battery" indicator as a notice to change the batteries. In some embodiments, four standard "AA" size battery cells can be used, as well known to those skilled in the art. This can be done by removing a cover, as shown in FIG. 15 to replace the batteries in the battery holder as shown in FIG. 16.

Figure 17:
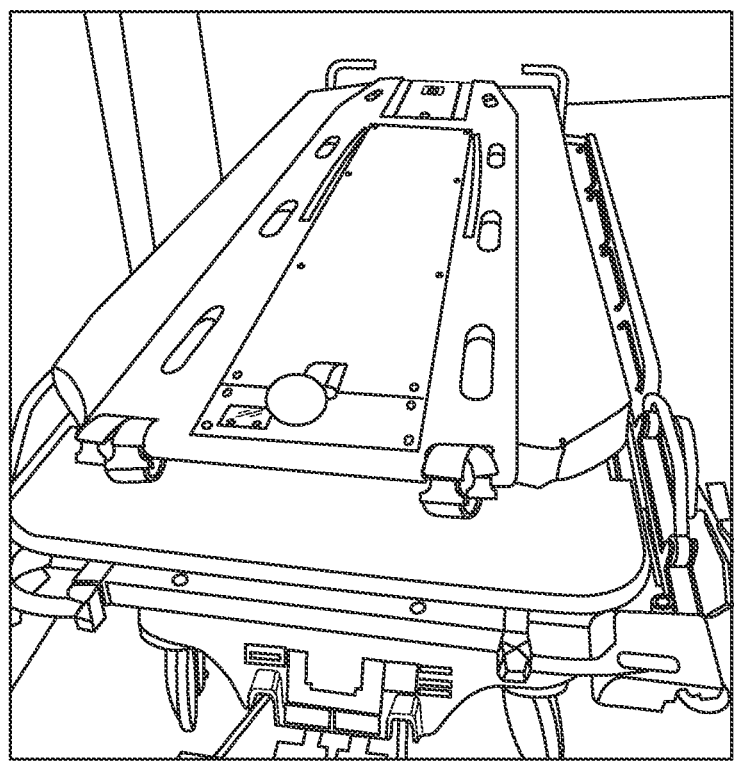
FIG. 17 is a perspective view depicting the spine board of FIG. 7 without a mattress placed on top thereof.
Figure 18:
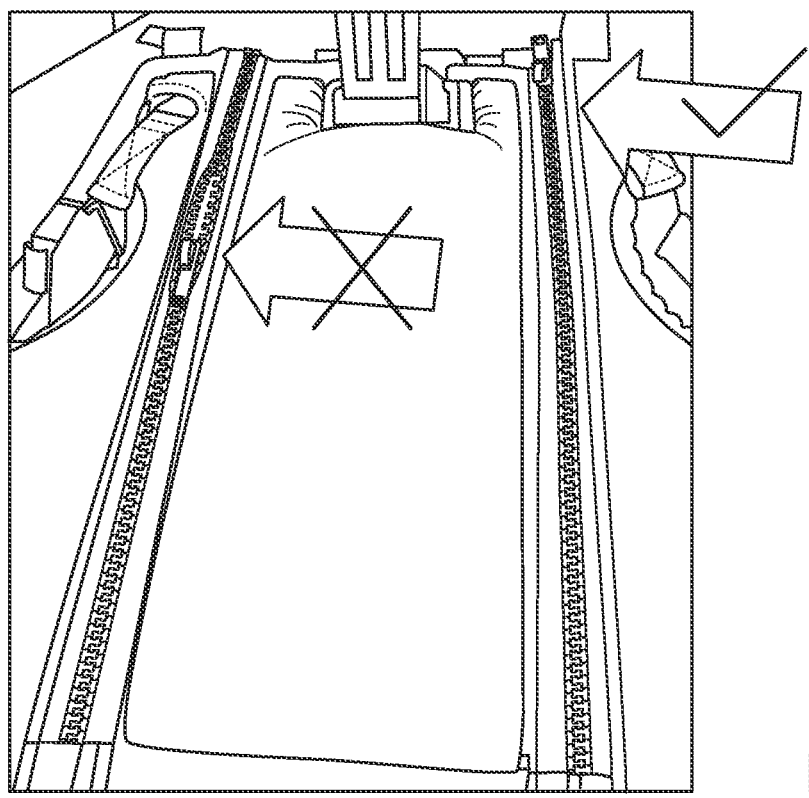
FIG. 18 is a perspective view depicting the skull tong anchor assembly installed in the spine board with a mattress placed thereon.
Figure 19:
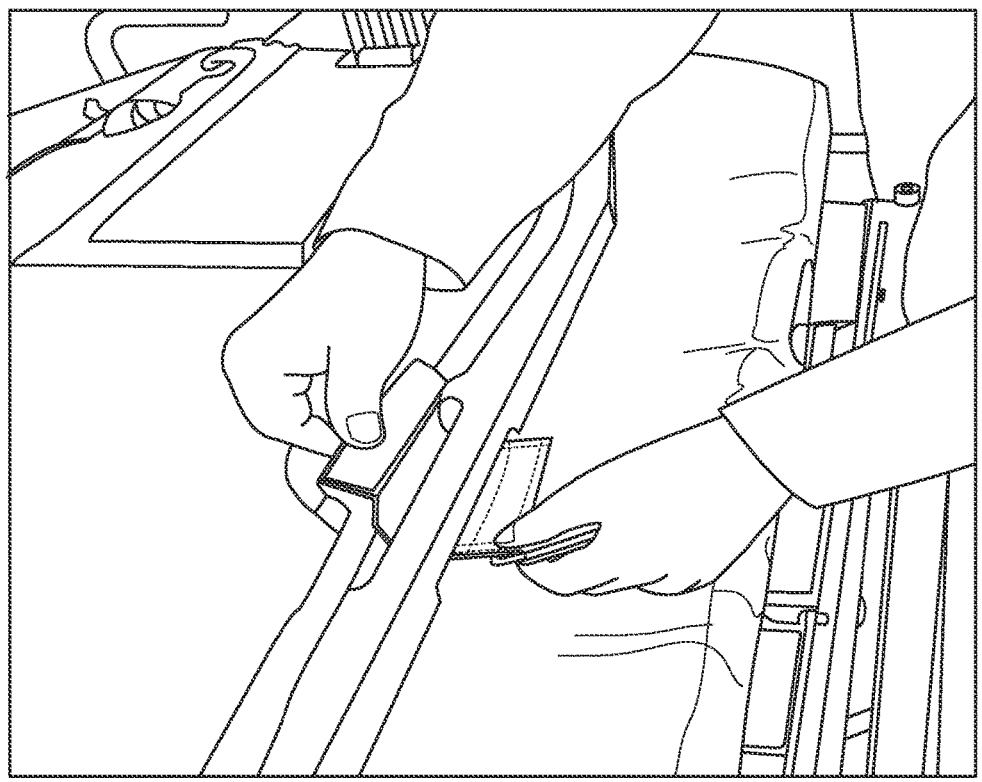
FIG. 19 is a perspective view depicting the spine board of FIG. 18 with the mattress being attached with Velcro™ straps placed through hand holds disposed in the spine board.
Figure 20:
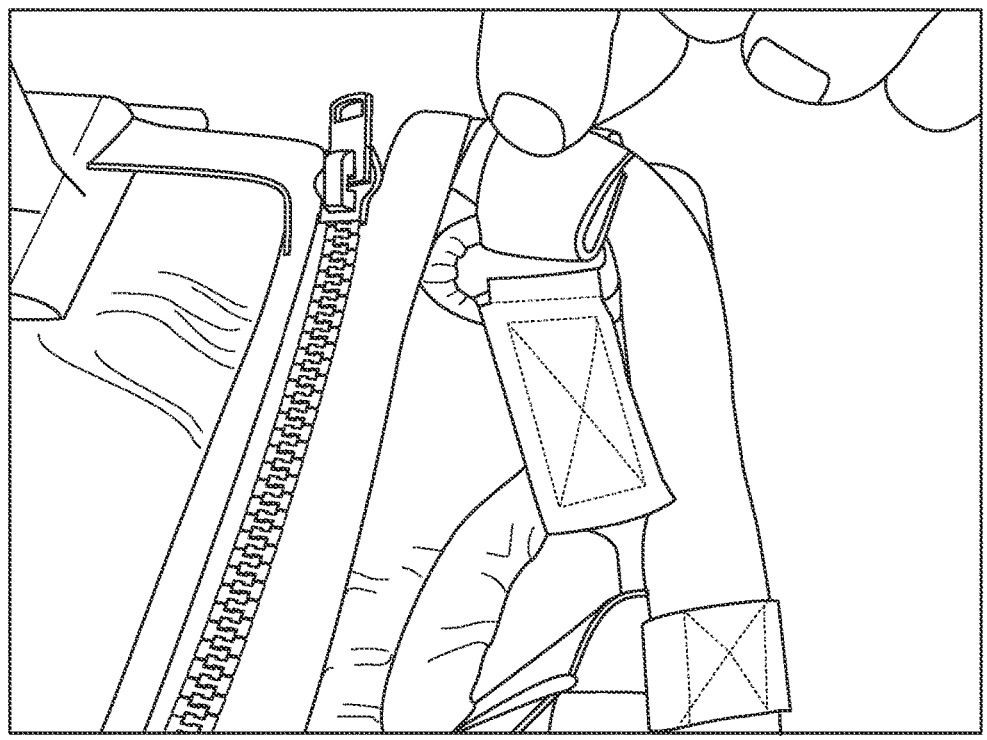
FIG. 20 is a perspective view depicting mattress straps being attached to a spine board near the skull tong anchor assembly.

Referring to FIG. 17, the spine board is shown placed on a stable stretcher prior to receiving a patient. Referring to FIG. 18, the mattress is shown on the spine board. Prior to a patient being placed onto the mattress, both zippers should be zipped up. Referring to FIGS. 19 and 20, the mattress can be secured to the spine board with Velcro™ straps passing through hand holds or openings disposed through the spine board. In some embodiments, there can be two straps at the upper or head end of the spine board and one on each side of the spine board.

Figure 21:
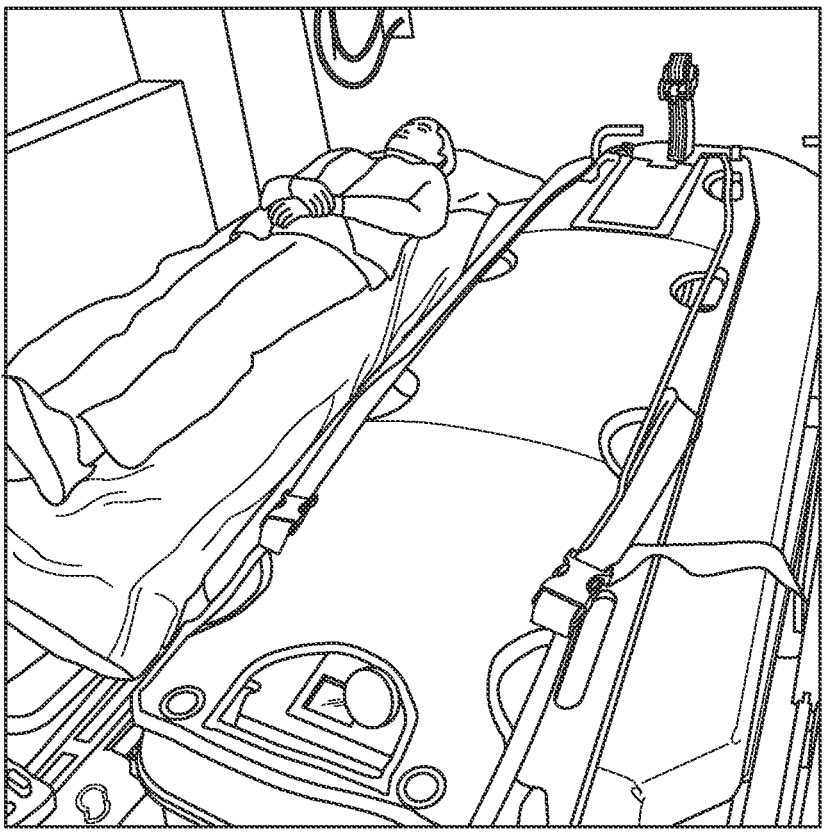
FIG. 21 is a perspective view depicting a patient about to be placed onto the spine board of FIG. 7 having a mattress placed thereon
Figure 22:
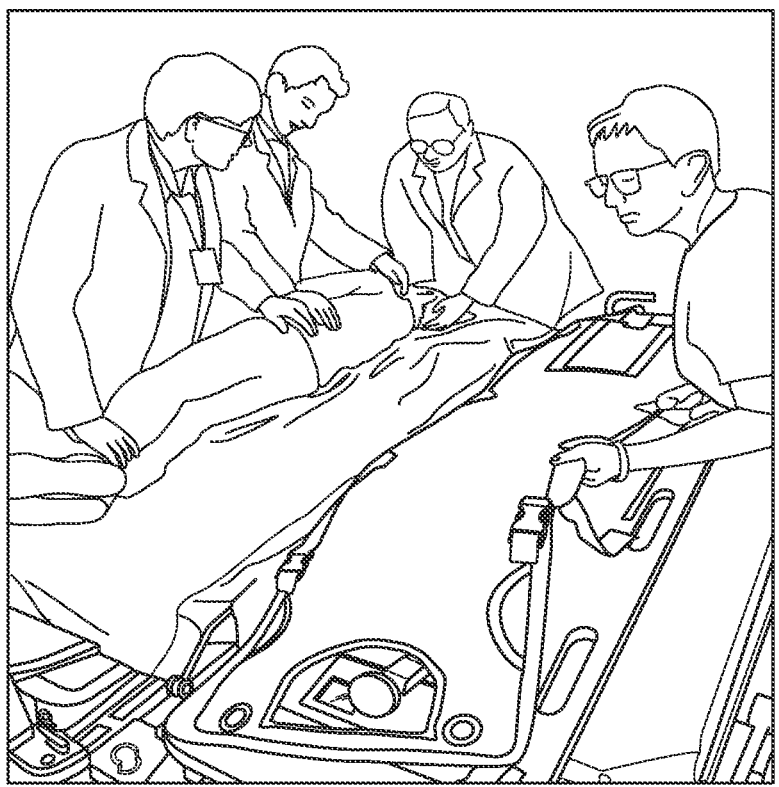
FIG. 22 is a perspective view depicting the mattress of FIG. 21 being placed beneath the back of the patient.
Figure 23:
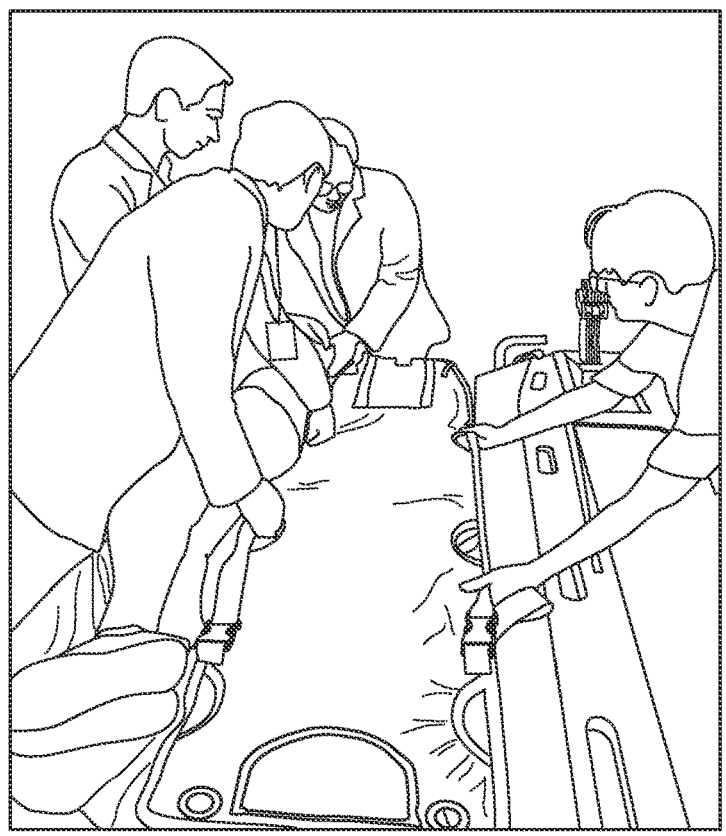
FIG. 23 is a perspective view depicting the patient of FIG. 22 being rolled onto the mattress.
Figure 24:
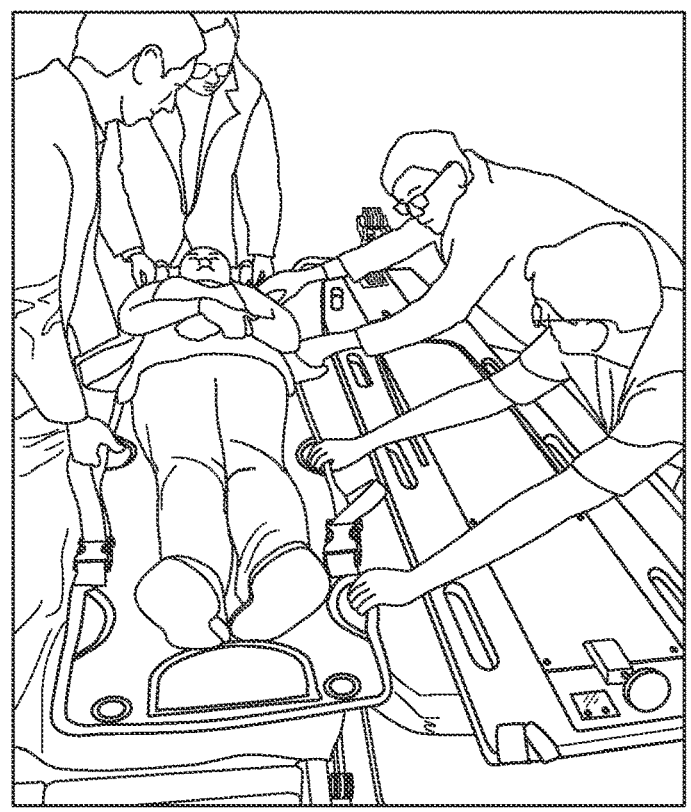
FIG. 24 is a perspective view depicting the patient of FIG. 23 placed on the mattress is preparation to be pulled onto the spine board of FIG. 7.
Figure 25:
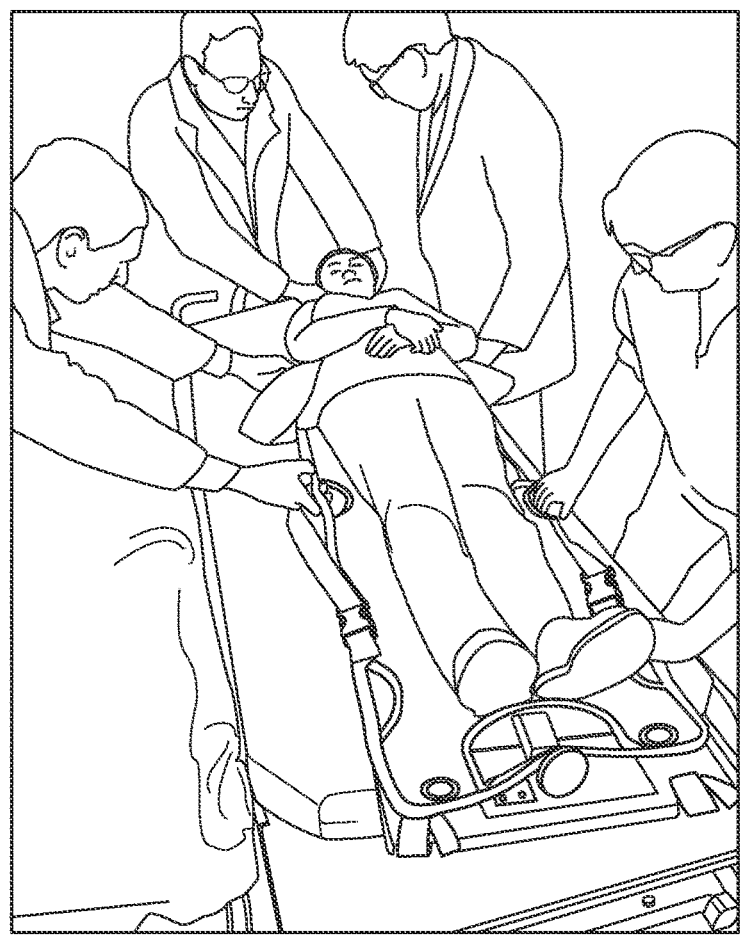
FIG. 25 is a perspective view depicting the patient of FIG. 24 placed on the spine board with the mattress being secured to the spine board with its Velcro™ straps.
Figure 26:
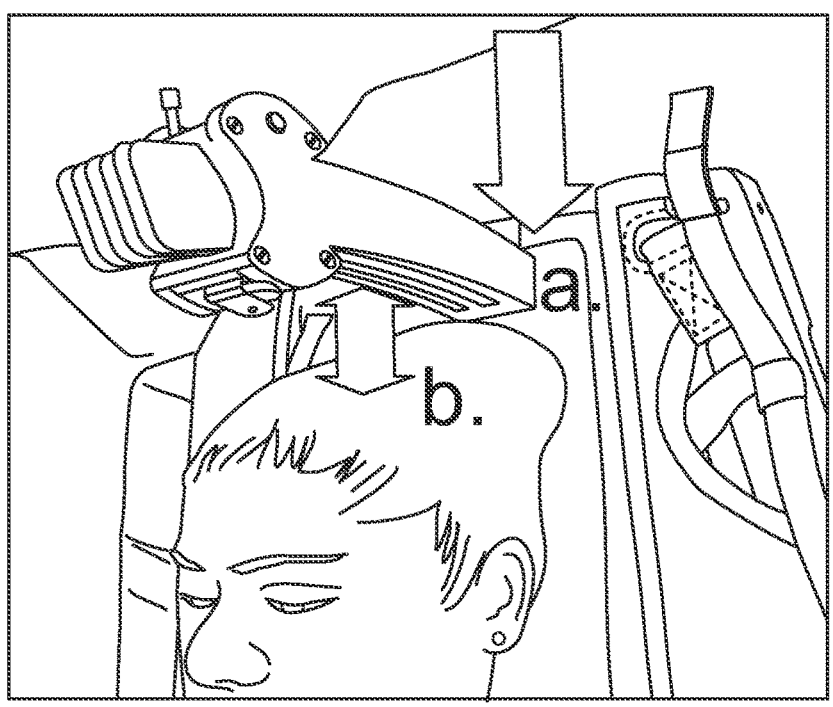
FIG. 26 is a perspective view depicting the placement of the head of the patient of FIG. 25 in relation to the skull tong anchor assembly.
Figure 27:
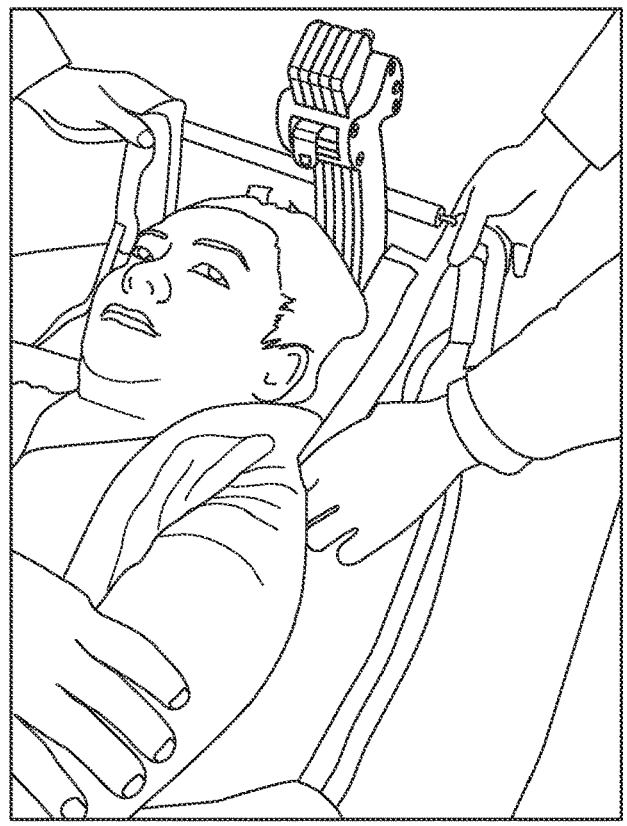
FIG. 27 is a perspective view depicting the mattress of FIG. 26 having shoulder straps being unzipped therefrom.
Figure 28:
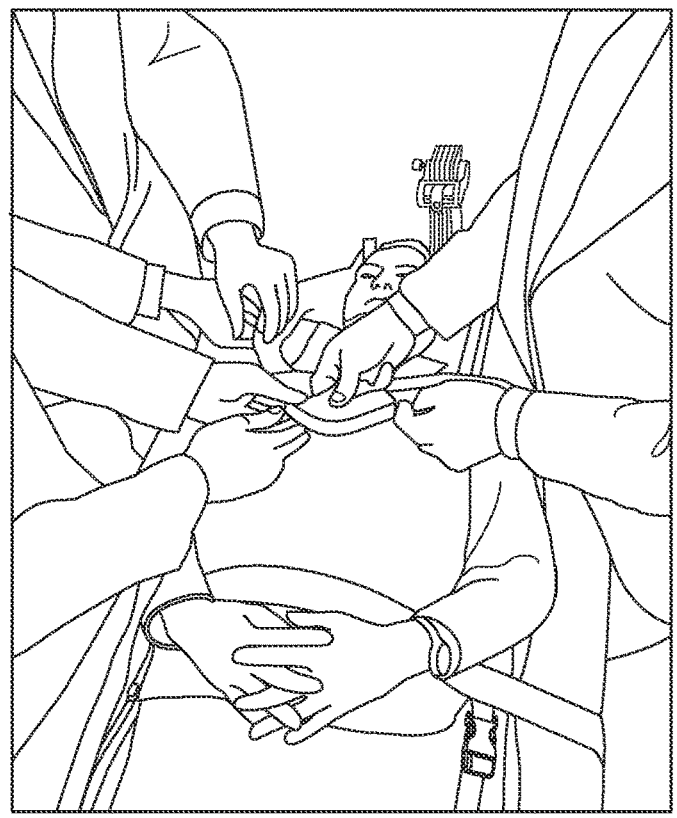
FIG. 28 is a perspective view depicting the patient of FIG. 26 being secured to the spine board with adjustable straps.
Figure 29:
FIG. 29 is a perspective view depicting the securing of shoulder straps to the patient of FIG. 28.

Referring to FIG. 21, a patient waiting to be transferred onto the spine board is shown. Referring to FIG. 22, the mattress can be unstrapped from the spine board before being placed underneath the patient who has been rolled to one side. Referring to FIG. 23, the mattress is placed beside the patient before being rolled onto the mattress, as shown in FIG. 24, where the patient can then be pulled onto the spine board by the hand holds on the mattress, as shown in FIG. 25. The mattress can be moved until it is aligned with the traction post, as shown in FIG. 26. At this point, the Velcro™ straps can be attached to the spine board, as described above.

Figure 30:
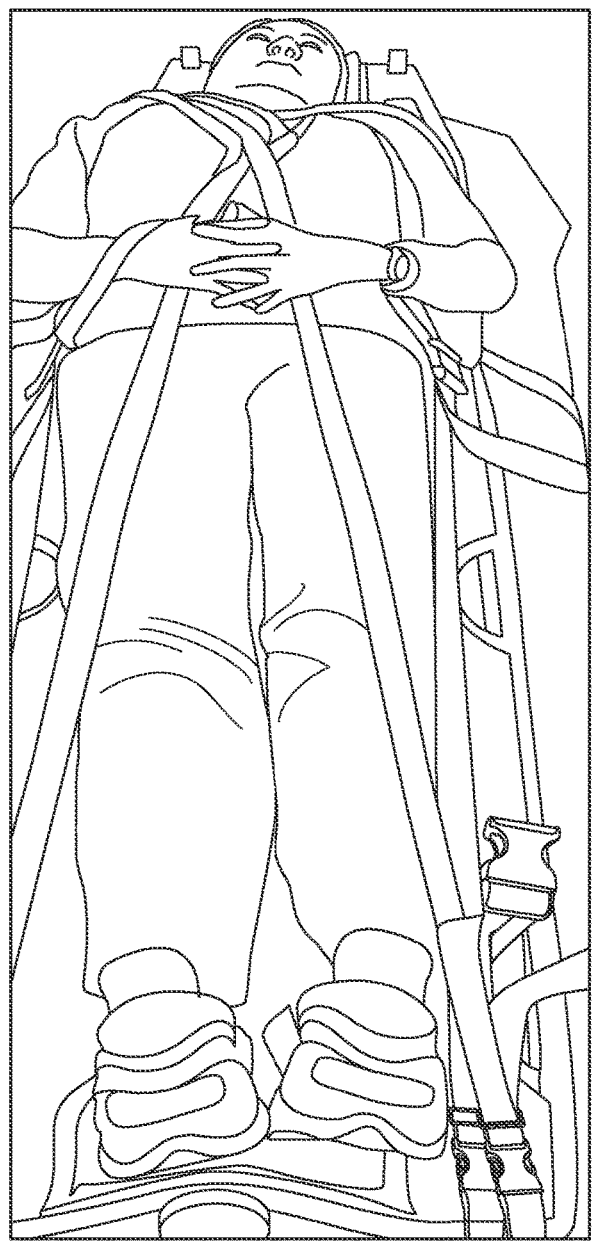
FIG. 30 is a perspective view depicting the patient of FIG. 29 with shoulder straps securing the patient to the spine board.
Figure 31:
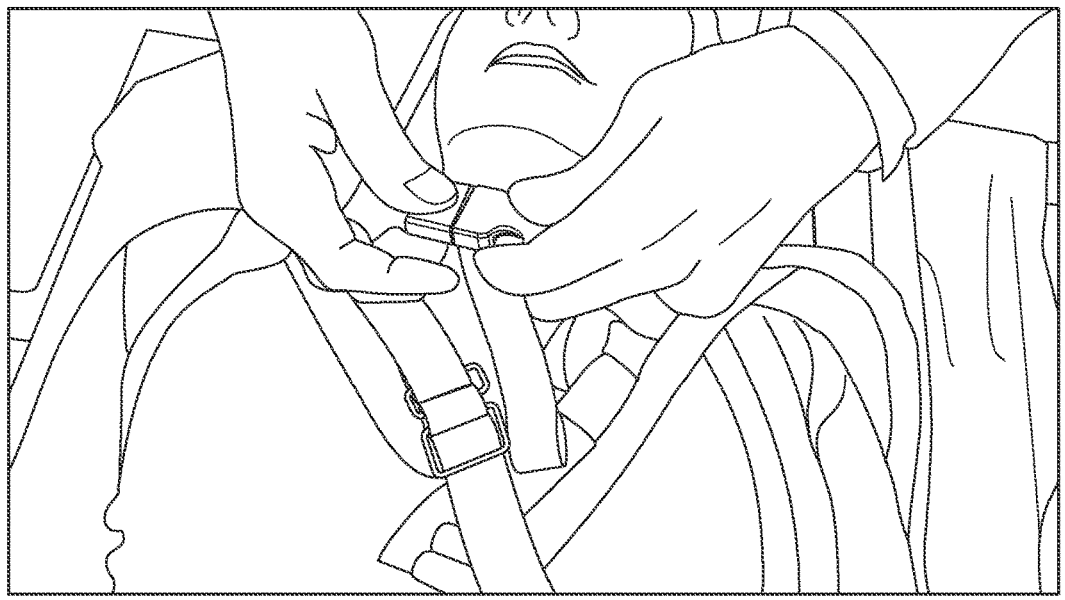
FIG. 31 is a perspective view depicting the shoulder straps of FIG. 30 being secured together.

Referring to FIGS. 27 to 31, the zippers on the mattress can be unzipped to release the shoulder straps from the mattress. In some embodiments, the shoulder straps can be placed over the shoulders and down the chest of the patient in an X-type configuration to couple with straps (shown as blue in the figure) attached to the lower or foot end of the spine board and adjusted so that they are snug fitting to the patient, as shown in FIG. 30. The shoulder straps can then be coupled to each other, as shown in FIG. 31.

Figure 32:
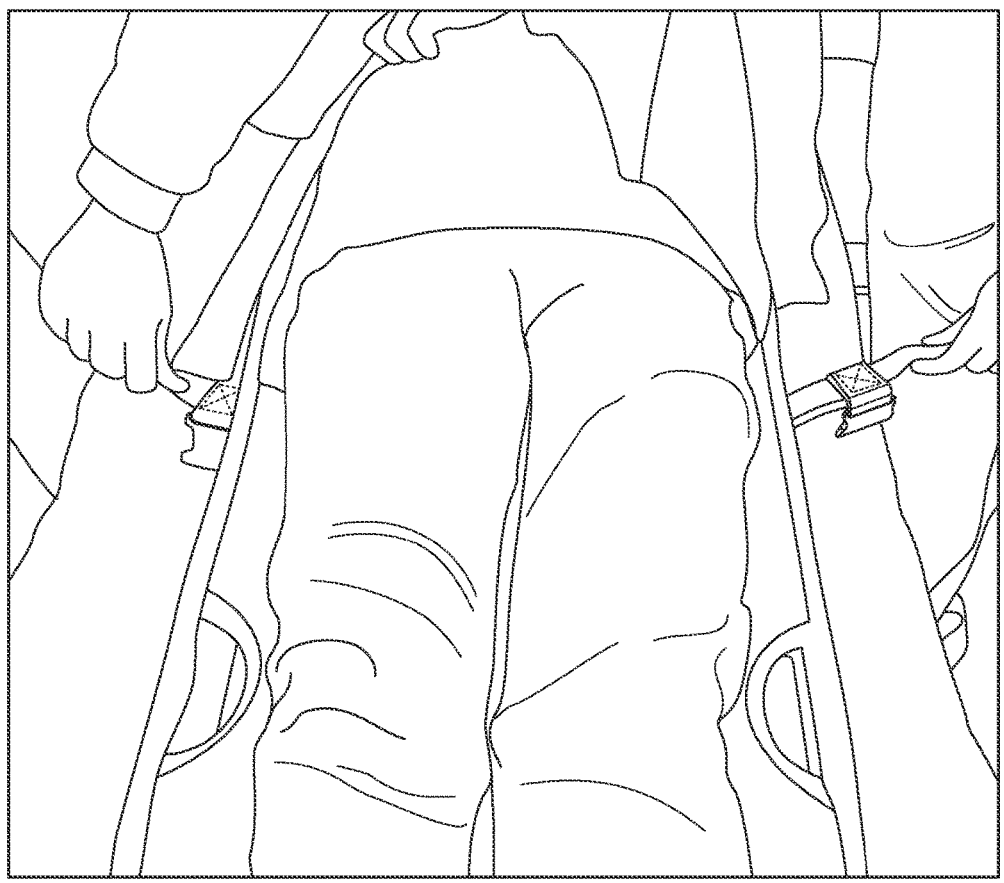
FIG. 32 is a perspective view depicting pelvic straps about to be placed on the patient of FIG. 31.
Figure 33:
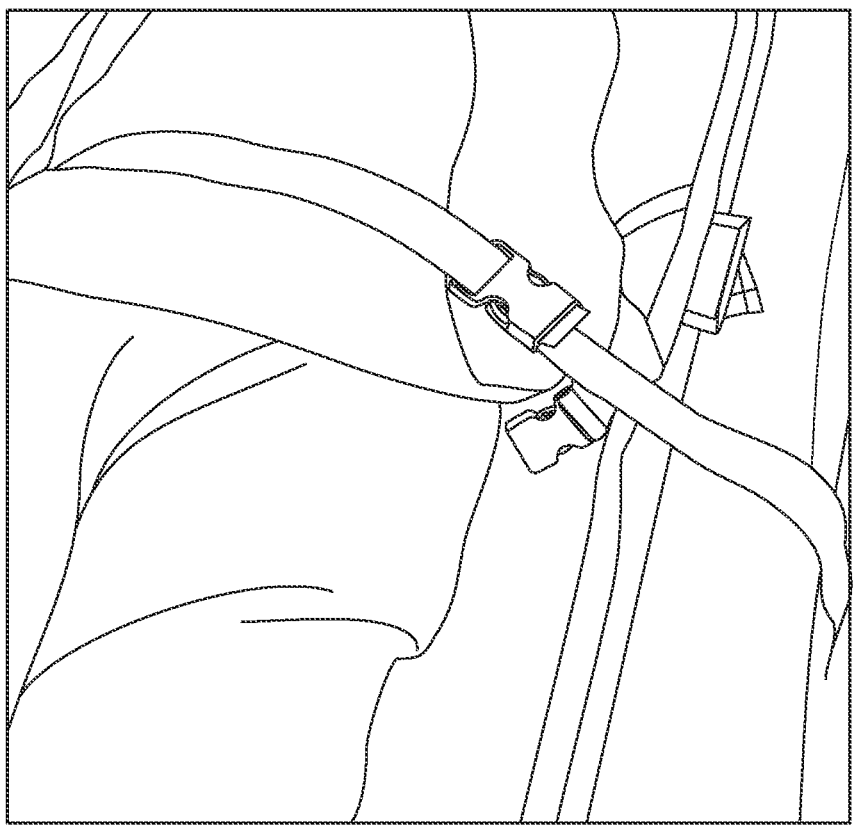
FIG. 33 is a perspective view depicting the pelvic strap of FIG. 32 secured to the patient.
Figure 34:
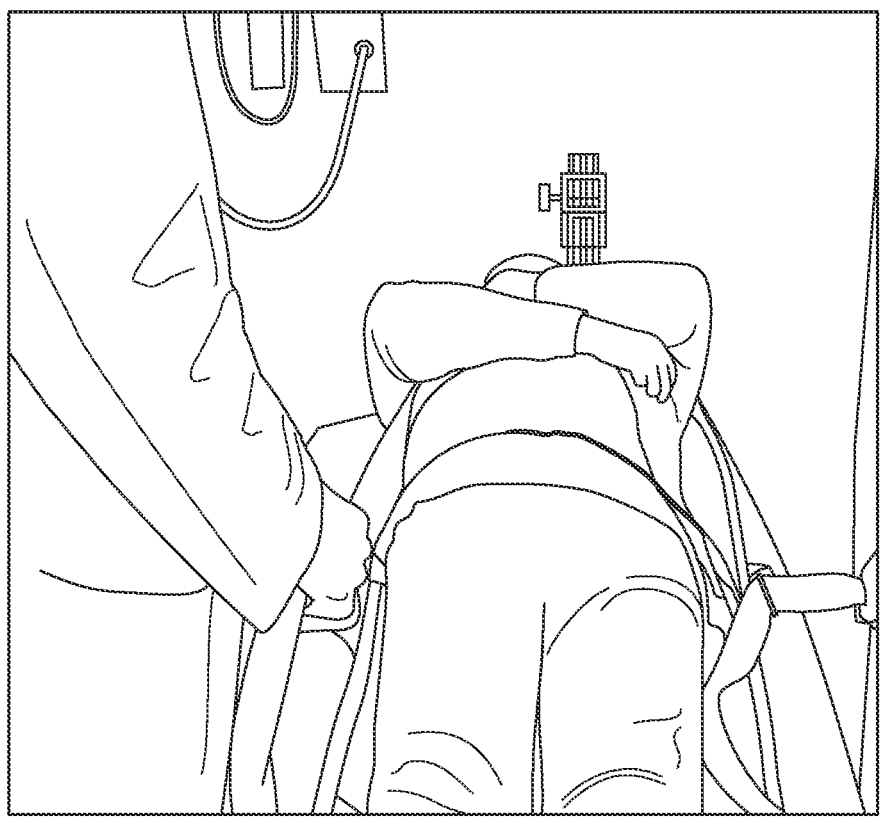
FIG. 34 is a perspective view depicting anchor straps being attached to the pelvic strap of FIG. 33.
Figure 35:
FIG. 35 is a perspective view depicting the anchor straps of FIG. 34 being secured to the foot end of the spine board.

Referring to FIGS. 32 and 33, a pelvic restraint belt can be placed across the abdomen of the patient and adjusted so that it is secured snuggly. Then straps (shown in yellow) can be attached to couple the pelvic restraint belt to a foot end buckle on each side of the patient, as shown in FIGS. 34 and 35. This belt and strap configuration can secure the lower portion of the patient to the spine board and anchor the patient when traction is applied to the patient.

Figure 36:
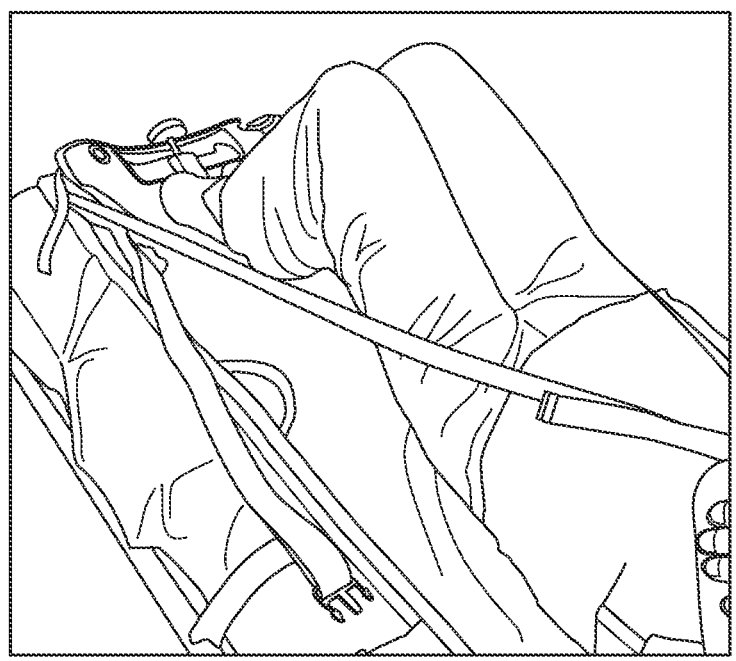
FIG. 36 is a perspective view depicting an alternative patient placement on the spine board where the patient's knees are bent.

Referring to FIG. 36, an alternate positioning of the patient on the spine board is shown, with the patient's knees in a bent position. In some embodiments, the spine board is no longer than 73 inches long to enable it to be placed in an ambulatory helicopter. Depending on the height of the patient, the patient's knees can be flexed sufficiently and supported by a cushion where the patient's heels can remain on the spine board and still fit within the space available in the ambulatory helicopter.

Figure 37:
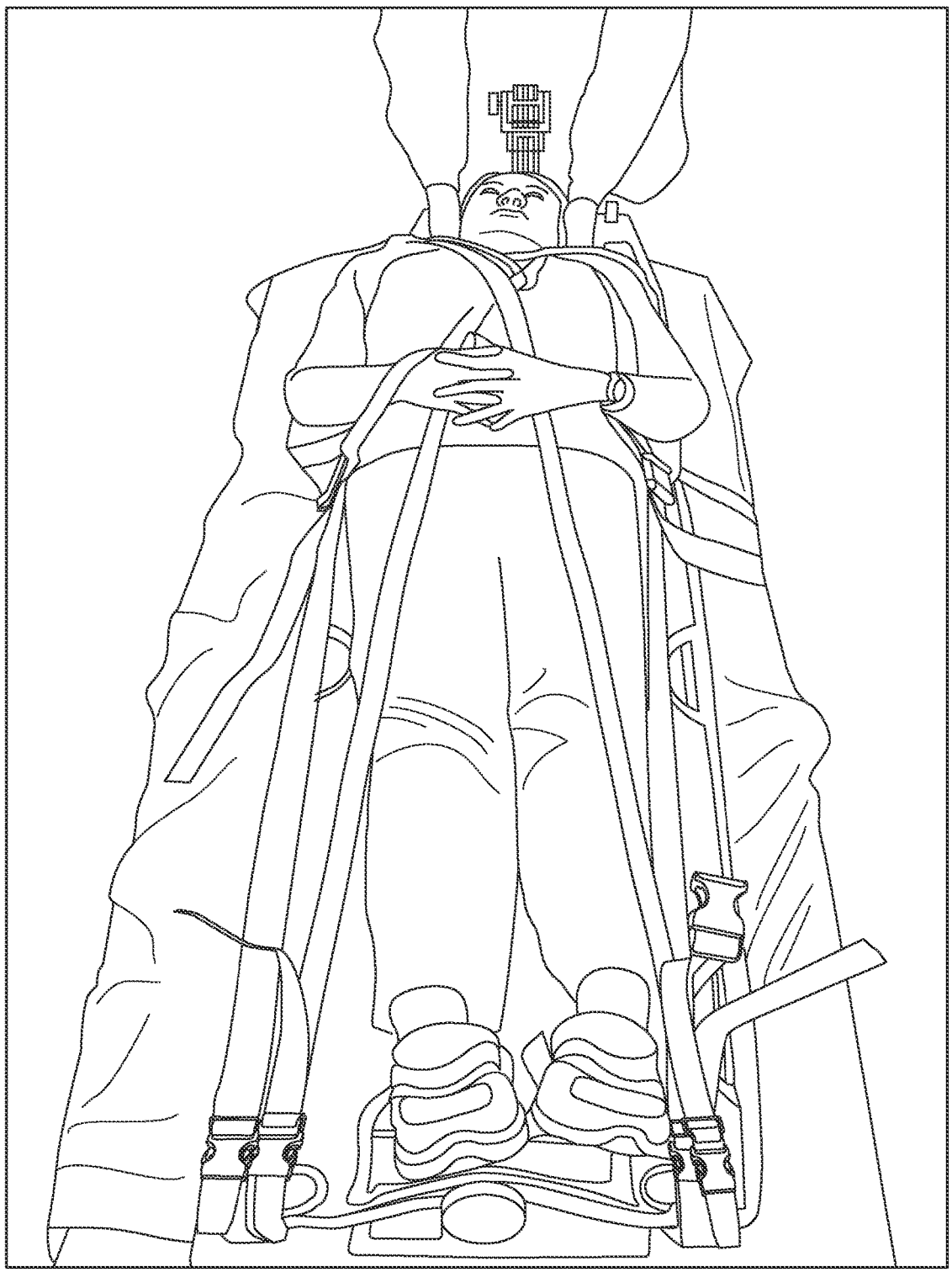
FIG. 37 is a perspective view depicting a final set up of the patient of FIG. 35 secured to the spine board.

When properly secured to the spine board, a patient will be attached with the shoulder straps and the pelvic restraint belt and straps as shown in FIG. 37.

Although a few embodiments have been shown and described, it will be appreciated by those skilled in the art that various changes and modifications can be made to these embodiments without changing or departing from their scope, intent or functionality. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

I claim:
1. A spine board, comprising:
   a) a back board further comprising a head board cavity disposed at a head end of the back board;
   b) a head board slidably disposed in the head board cavity;
   c) a skull tong anchor assembly disposed on the head board;
   d) a traction control assembly disposed at a foot end of the back board; and
   e) at least one push rod operatively coupling the traction control assembly to the head board wherein the combination of the traction control assembly and the at least one push rod is configured to slidably extend and retract the head board within the head board cavity.

2. The spine board as set forth in claim 1, further comprising track rails disposed in the head board cavity wherein the head board is slidably disposed within the track rails.

3. The spine board as set forth in claim 1, wherein the skull tong anchor assembly comprises a post and a traveler block movably disposed on the post.

4. The spine board as set forth in claim 3, wherein the skull tong anchor assembly further comprises a rack and pinion gear mechanism operatively coupling the traveler block to the post.

5. The spine board as set forth in claim 3, wherein the post is curved in configuration.

6. The spine board as set forth in claim 3, wherein the traveler block comprises a skull tong ring.

7. The spine board as set forth in claim 1, wherein the traction control assembly comprises:
   a) a support block disposed on the back board, the support block further comprising a threaded hole extending therethrough;
   b) a threaded rod disposed in the threaded hole;
   c) a control knob disposed on a first end of the threaded rod; and
   d) a U-joint mechanism disposed on a second end of the threaded rod, the U-joint mechanism operatively coupling the second end to the at least one push rod.

8. The spine board as set forth in claim 1, wherein the at least one push rod is disposed in a push rod cavity disposed in the back board.

9. The spine board as set forth in claim 8, further comprising a first cover configured to cover the push rod cavity.

10. The spine board as set forth in claim 1, wherein the at least one push rod comprises:
    a) a lower push rod operatively coupled to the traction control assembly;
    b) an upper push rod operatively coupled to the head board; and
    c) a strain gauge operatively coupling the upper push rod to the lower push rod.

11. The spine board as set forth in claim 10, wherein the strain gauge comprises an S-type load cell.

12. The spine board as set forth in claim 10, further comprising an electronic display unit operatively coupled to the strain gauge, the electronic display unit configured to visually display traction force applied to the head board by the traction control assembly.

13. The spine board as set forth in claim 12, wherein the electronic display unit is disposed in a display cavity disposed in the back board.

14. The spine board as set forth in claim 13, further comprising at least one battery operatively coupled to the electronic display unit, the at least one battery disposed in a battery cavity disposed in the back board.

15. The spine board as set forth in claim 14, further comprising a second cover configured to cover the display cavity and the battery cavity.

16. The spine board as set forth in claim 1, further comprising a mattress releasably attached to the back board with at least one strap coupled to a corresponding hand hole disposed through the back board.

17. The spine board as set forth in claim 16, wherein the mattress comprises shoulder straps configured to partially detach from the mattress, the shoulder straps configured to operatively couple to the foot end of the back board.

18. The spine board as set forth in claim 16, wherein the mattress further comprises a pelvic restraint belt.

19. The spine board as set forth in claim 18, further comprising at least one pelvic restraint anchor strap operatively coupling the pelvic restraint belt to the foot end of the back board.

\* \* \* \* \*